(12) United States Patent
Perry

(10) Patent No.: US 6,700,395 B1
(45) Date of Patent: Mar. 2, 2004

(54) SOIL MOISTURE INDICATOR DEVICE

(76) Inventor: Betty J. Perry, 30 Stockton Ct., Morris Plains, NJ (US) 07950

( * ) Notice: Subject to any disclaimer, the term of this patent is extended or adjusted under 35 U.S.C. 154(b) by 0 days.

(21) Appl. No.: 10/133,273

(22) Filed: Apr. 26, 2002

(51) Int. Cl.[7] .......................... G01R 27/02; G08B 21/00
(52) U.S. Cl. ................... 324/696; 324/664; 324/694; 73/73; 340/602
(58) Field of Search ................. 73/73; 702/1, 2, 702/25, 50, 55, 183, FOR 115, 116, 127, 134, 170; 324/664, 694, 689, 696, 445, 446, 690; 340/500, 602

(56) References Cited

U.S. PATENT DOCUMENTS

| | | | |
|---|---|---|---|
| 3,882,383 A | 5/1975 | Matlin | 324/696 |
| 3,979,667 A | 9/1976 | Cornes | 324/694 |
| 4,020,417 A | 4/1977 | Brehob et al. | 324/694 |
| 4,122,389 A | 10/1978 | Haagen | 324/694 |
| 4,268,824 A | 5/1981 | Phillips | 340/604 |
| D426,473 S | 6/2000 | Blackburn | D10/56 |
| 6,198,398 B1 * | 3/2001 | Velasquez | 340/604 |

\* cited by examiner

*Primary Examiner*—N. Le
*Assistant Examiner*—Vincent Q. Nguyen

(57) ABSTRACT

A soil moisture indicator device for alerting a user when the soil in a pot needs to be watered to sustain a plant. The soil moisture indicator device includes a body member having a first end and a second end. The first end of the body member is designed for being inserted into the soil of the pot. A sensing elements is designed for sensing the relative moisture of the soil in at the pot. The sensing elements is positioned in the body member whereby the sensing elements is designed for being submerged into the soil when the body member is inserted into the soil. A low moisture light is operationally coupled to the sensing elements. The low moisture light emits light when the sensing elements detects the moisture in the soil being greater than a predetermined dry level.

8 Claims, 2 Drawing Sheets

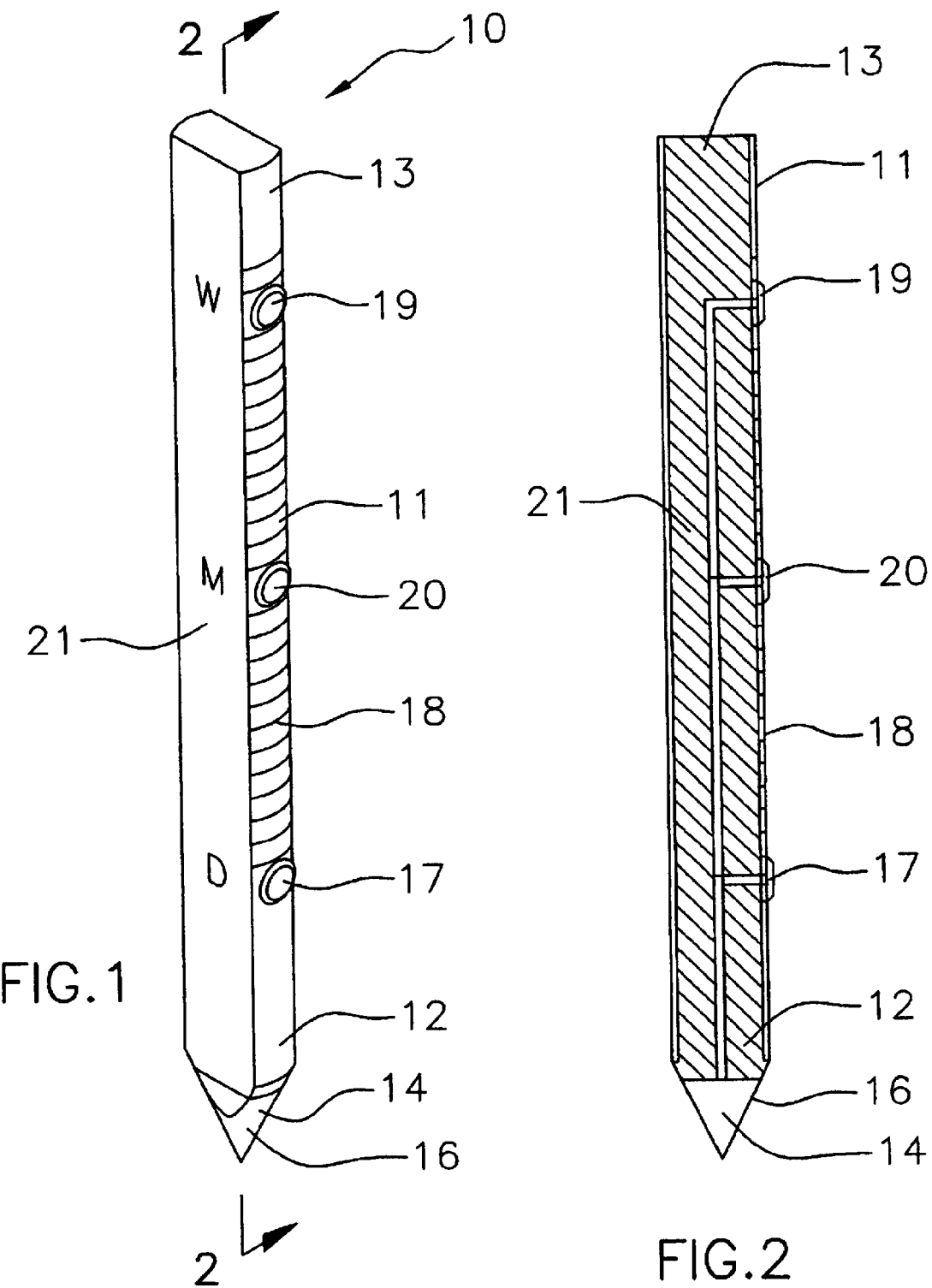

SOIL MOISTURE INDICATOR DEVICE

BACKGROUND OF THE INVENTION

1. Field of the Invention

The present invention relates to plant moisture level signaling devices and more particularly pertains to a new soil moisture indicator device for alerting a user when the soil in a pot needs to be watered to sustain a plant.

2. Description of the Prior Art

The use of plant moisture level signaling devices is known in the prior art. U.S. Pat. No. 4,268,824 describes a device for sensing the amount of moisture in the soil. Another type of plant moisture level signaling device is U.S. Pat. No. 4,020,417 having a soil moisture indicator device lighting one of a pair lights in response to the amount of moisture in the soil. U.S. Pat. No. Des. 426,473 shows a moisture detector. U.S. Pat. No. 3,979,667 has a soil moisture indicator for lighting one of pair lights in response to the amount of moisture in the soil. U.S. Pat. No. 3,88,383 has a soil moisture sensing system for determining the amount of moisture in the soil.

While these devices fulfill their respective, particular objectives and requirements, the need remains for a device that has certain improved features for indicating to the user a level moisture in the soil.

SUMMARY OF THE INVENTION

The present invention meets the needs presented above by providing a low moisture light, an adequate moisture light and a high moisture indicator for indicating a relative level moisture of the soil in the pot.

Still yet another object of the present invention is to provide a new soil moisture indicator device that indicates a relative level of moisture in the soil.

To this end, the present invention generally comprises a body member having a first end and a second end. The first end of the body member is designed for being inserted into the soil of the pot. The first end of the body member is tapered for facilitating insertion of the first end of the body member into the soil the pot. A sensing means is designed for sensing the relative moisture of the soil in the pot. The sensing means is positioned in the body member adjacent the first end of the body member whereby the sensing means is designed for being submerged into the soil when the first end of the body member is inserted into the soil. A power supply is operationally coupled to the sensing means whereby the power supply supplies power to the sensing means. An outer surface of said sensing means being exposed to the soil of the pot to allow the sensor to detect the level of moisture in the soil. A low moisture light is operationally coupled to the sensing means. The low moisture light emits light when the sensing means detects the moisture in the soil being greater than a predetermined dry level. The low moisture light is positioned along a front face of the body member whereby the low moisture light is designed for being viewed by a user. The low moisture light is positioned proximate the first end of the body member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new soil moisture indicator device according to the present invention.

FIG. 2 is a cross-sectional view of the present invention.

DESCRIPTION OF THE PREFERRED EMBODIMENT

Figure 3:
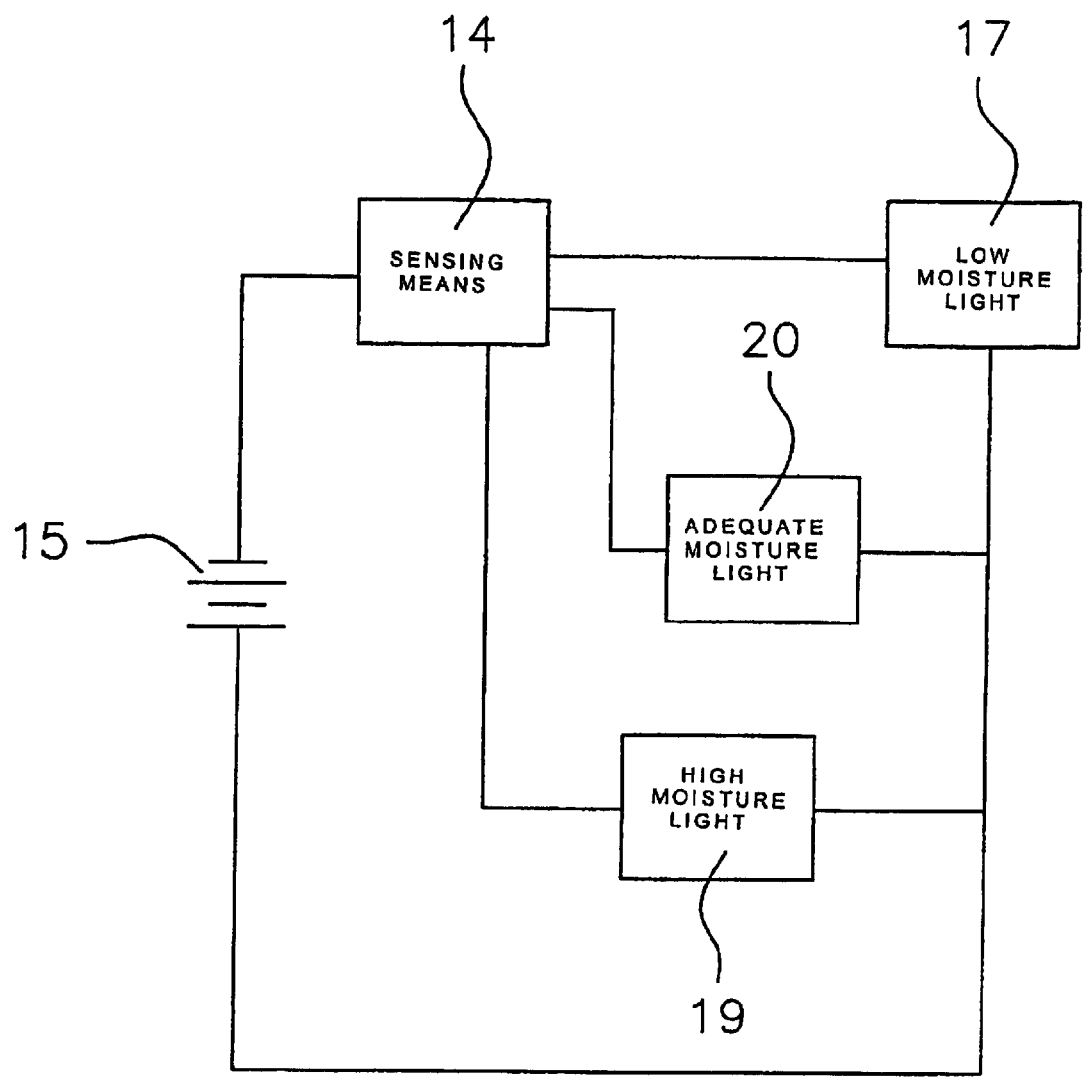
FIG. 3 is a schematic view of the present invention.

With reference now to the drawings, and in particular to FIGS. 1 through 3 thereof, a new soil moisture indicator device embodying the principles and concepts of the present invention and generally designated by the reference numeral 10 will be described.

As best illustrated in FIGS. 1 through 3, the soil moisture indicator device 10 generally comprises a body member 11 having a first end 12 and a second end 13. The first end 12 of the body member 11 is designed for being inserted into the soil of the pot. The first end 12 of the body member 11 is tapered for facilitating insertion of the first end 12 of the body member 11 into the soil of the pot.

A sensing means 14 is designed for sensing the relative moisture of the soil in the pot. The sensing means 14 is positioned in the body member 11 adjacent the first end 12 of the body member 11 whereby the sensing means 14 is designed for being submerged into the soil when the first end 12 of the body member 11 is inserted into the soil. A power supply 15 is operationally coupled to the sensing means 14 whereby the power supply 15 supplies power to the sensing means 14. An outer surface 16 of said sensing means 14 being exposed to the soil of the pot to allow the sensor to detect the level of moisture in the soil.

A low moisture light 17 is operationally coupled to the sensing means 14. The low moisture light 17 emits light when the sensing means 14 detects the moisture in the soil being greater than a predetermined dry level. The low moisture light 17 is positioned along a front face 18 of the body member 11 whereby the low moisture light 17 is designed for being viewed by a user. The low moisture light 17 is positioned proximate the first end 12 of the body member 11.

A high moisture light 19 is operationally coupled to the sensing means 14. The high moisture light 19 emits light when the sensing means 14 detects the moisture in the soil being greater than a predetermined saturated level. The high moisture light 19 is positioned along the front face 18 of the body member 11 whereby the high moisture light 19 is designed for being viewed by the user. The high moisture light 19 is positioned proximate the second end 13 of the body member 11.

An adequate moisture light 20 is operationally coupled to the sensing means 14. The adequate moisture light 20 emits light when the sensing means 14 detects the moisture in the soil being greater than a predetermined adequate level. The predetermined adequate level has a value between the predetermined dry level and the predetermined high level. The adequate moisture light 20 is positioned on the front face 18 of the body member 11 whereby the adequate moisture light 20 is designed for being viewed by the user. The adequate moisture light 20 is positioned along a medial portion 21 of the body member 11 whereby the adequate moisture light 20 is positioned between the low moisture light 17 and the high moisture light 19.

In use, the user inserts the body member II into the soil of the pot. The sensing means 14 senses the amount moisture in the soils. The sensing means 14 lights the low moisture light 17, the adequate moisture light 20 and the high moisture light 19 when the moisture in the soil is greater than the predetermined saturated level. The sensing means 14 lights the low moisture light 17 and the adequate moisture light 20 when the moisture in the soil is greater than the predetermined adequate level. The sensing means 14 lights the low moisture light 17 when the moisture in the soil is greater than the predetermined dry level. The low moisture light 17 fails to emit light when the sensing means 14 fails to sense the moisture in the soil being greater than the predetermined dry level thereby indicating that the user needs to water the plant in the soil.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A soil moisture indicator device for indicating the amount of moisture in the soil of a pot, the soil moisture indicator device comprising:
   a body member having a first end and a second end, said first end of said body member being adapted for being inserted into the soil of the pot;
   a sensing means being adapted for sensing the relative moisture of the soil in the pot, said sensing means being positioned in said body member adjacent said first end of said body member such that said sensing means is adapted for being submerged into the soil when said first end of said body member is inserted into the soil, a power supply being operationally coupled to said sensing means such that said power supply supplies power to said sensing means;
   a low moisture light being operationally coupled to said sensing means, said low moisture light emitting light when said sensing means detects the moisture in the soil greater than a predetermined dry level, said low moisture light being positioned along a front face of said body member such that said low moisture light is adapted for being viewed by a user; and
   an indicator indicia being positioned on an exterior surface of said body member, said indicator indicia being for indicating the significance of said low moisture light when said low moisture light is emitting light.

2. The soil moisture indicator device as set forth in claim 1, wherein said low moisture light is positioned proximate said first end of said body member.

3. The soil moisture indicator device as set forth in claim 1, further comprising:
   a high moisture light being operationally coupled to said sensing means, said high moisture light emitting light when said sensing means detects the moisture in the soil greater than a predetermined saturated level, said high moisture light being positioned along said front face of said body member such that said high moisture light is adapted for being viewed by the user.

4. The soil moisture indicator device as set forth in claim 3, wherein said high moisture light is positioned proximate said second end of said body member.

5. The soil moisture indicator device as set forth in claim 3, further comprising:
   an adequate moisture light being operationally coupled to said sensing means, said adequate moisture light emitting light when said sensing means detects the moisture in the soil being greater than a predetermined adequate level, said predetermined adequate level having a value between said predetermined dry level and said predetermined high level, said adequate moisture light being positioned on said front face of said body member such that said adequate moisture light is adapted for being viewed by the user.

6. The soil moisture indicator device as set forth in claim 5, wherein said adequate moisture light is positioned along a medial portion of said body member such that said adequate moisture light is positioned between said low moisture light and said high moisture light.

7. The soil moisture indicator device as set forth in claim 1, wherein said first end of said body member is tapered for facilitating insertion of said first end of said body member into the soil of the pot.

8. A soil moisture indicator device for indicating the amount of moisture in the soil of a pot, the soil moisture indicator device comprising:
   a body member having a first end and a second end, said first end of said body member being adapted for being inserted into the soil of the pot;
   a sensing means being adapted for sensing the relative moisture of the soil in the pot, said sensing means being positioned in said body member adjacent said first end of said body member such that said sensing means is adapted for being submerged into the soil when said first end of said body member is inserted into the soil, a power supply being operationally coupled to said sensing means such that said power supply supplies power to said sensing means;
   a low moisture light being operationally coupled to said sensing means, said low moisture light emitting light when said sensing means detects the moisture in the soil greater than a predetermined dry level, said low moisture light being positioned along a front face of said body member such that said low moisture light is adapted for being viewed by a user;
   said low moisture light being positioned proximate said first end of said body member;
   a high moisture light being operationally coupled to said sensing means, said high moisture light emitting light when said sensing means detects the moisture in the soil greater than a predetermined saturated level, said high moisture light being positioned along said front face of said body member such that said high moisture light is adapted for being viewed by the user;
   said high moisture light being positioned proximate said second end of said body member;

an adequate moisture light being operationally coupled to said sensing means, said adequate moisture light emitting light when said sensing means detects the moisture in the soil being greater than a predetermined adequate level, said predetermined adequate level having a value between said predetermined dry level and said predetermined high level, said adequate moisture light being positioned on said front face of said body member such that said adequate moisture light is adapted for being viewed by the user;

said adequate moisture light being positioned along a medial portion of said body member such that said adequate moisture light is positioned between said low moisture light and said high moisture light;

said first end of said body member being tapered for facilitating insertion of said first end of said body member into the soil of the pot, and an indicator indicia being Positioned on an exterior surface of said body member said indicator indicia being for indicating the significance of said low moisture light when said low moisture light is emitting light.

* * * * *